(12) United States Patent
Honda et al.

(10) Patent No.: US 8,623,434 B2
(45) Date of Patent: Jan. 7, 2014

(54) ASTAXANTHIN-CONTAINING PET FOODS

(75) Inventors: Tomoaki Honda, Aichi-ken (JP); Jiro Takahashi, Toyama-ken (JP)

(73) Assignee: Fuji Chemical Industry Co., Ltd., Toyama-Ken (JP)

( * ) Notice: Subject to any disclaimer, the term of this patent is extended or adjusted under 35 U.S.C. 154(b) by 0 days.

(21) Appl. No.: 12/962,088

(22) Filed: Dec. 7, 2010

(65) Prior Publication Data
US 2011/0077307 A1    Mar. 31, 2011

Related U.S. Application Data

(63) Continuation of application No. 10/583,482, filed as application No. PCT/JP2004/018950 on Dec. 17, 2004, now abandoned.

(30) Foreign Application Priority Data

Dec. 19, 2003  (JP) .................................. 2003-422304

(51) Int. Cl.
*A23K 1/18* (2006.01)

(52) U.S. Cl.
USPC ................................ 426/2; 426/805; 426/807

(58) Field of Classification Search
USPC ................................ 426/2, 73, 635, 805, 807
See application file for complete search history.

(56) References Cited

U.S. PATENT DOCUMENTS

| | | | |
|---|---|---|---|
| 5,527,533 A | 6/1996 | Tso et al. | |
| 5,937,790 A | 8/1999 | Ito et al. | |
| 6,022,867 A | 2/2000 | Ito et al. | |
| 6,054,491 A * | 4/2000 | Lignell et al. | 514/725 |
| 6,086,886 A * | 7/2000 | Guo | 424/195.17 |
| 6,262,316 B1 * | 7/2001 | Wadstrom et al. | 568/834 |
| 6,265,450 B1 | 7/2001 | Asami et al. | |
| 6,923,967 B1 * | 8/2005 | Lignell | 424/195.17 |
| 7,001,611 B2 | 2/2006 | Kiso et al. | |
| 2003/0035821 A1 | 2/2003 | Heaton et al. | |
| 2003/0104090 A1 | 6/2003 | Levy et al. | |
| 2003/0124230 A1 | 7/2003 | Zielinski | |
| 2003/0170328 A1 * | 9/2003 | Haines et al. | 424/752 |
| 2004/0151761 A1 * | 8/2004 | Chew et al. | 424/442 |
| 2004/0170667 A1 | 9/2004 | Hayasaka et al. | |
| 2004/0234579 A1 * | 11/2004 | Finke | 424/442 |

FOREIGN PATENT DOCUMENTS

| | | | |
|---|---|---|---|
| CN | 101095698 A * | 1/2008 | |
| EP | 0088621 A2 | 9/1993 | |
| EP | 0088621 A3 | 9/1993 | |
| JP | 58-201715 A | 11/1983 | |
| JP | 3-266943 A | 11/1991 | |
| JP | 5-192087 A | 8/1993 | |
| JP | 7-196493 A | 8/1995 | |
| JP | 9-124470 A | 5/1997 | |
| JP | 10-175866 A | 6/1998 | |
| JP | 10-276721 A | 10/1998 | |
| JP | 2000-507821 A | 6/2000 | |
| JP | 2000-309545 A | 11/2000 | |
| JP | 2001-258480 A | 9/2001 | |
| JP | 2002-114690 A | 4/2002 | |
| WO | 9837874 A1 | 9/1998 | |
| WO | 0187291 A1 | 11/2001 | |
| WO | 02094253 A1 | 11/2002 | |
| WO | 03013268 A1 | 2/2003 | |

OTHER PUBLICATIONS

"GNC Pets Ultra Mega Cat FreshTM ", downloaded from www.gnc.com/product, dated Jan. 31, 2001, 2 pages.*
"Carrot", downloaded from www.anagen.net/carrot.htm, dated Jan. 31, 2001, 4 pages.*
Lorenzo , "A Review of Spirulina as a Carotenoid and Vitamin Source for Cultured Shrimp", downloaded from www. algaeart.biz, dated Nov. 30, 1998, 4 pages.*
"GNC Pets Ultra Mega Cat FreshTM " downloaded from www.gnc.com/product, dated Jan. 31, 2001, 2 pages.*
El Baky et al. (Biotechnology, vol. 2, No. 3, pp. 222-240, 2003.*
"Basic Information About Astaxanthin" downloaded from www.ehealthyshopper.com, dated Jun. 1996, 6 pages.*
"Carrot" downloaded from www.anagen.net/carrot.htm, dated Jan. 31, 2001, 4 pages.*
"Drink Carrot Juice", downloaded from www. lingy.net/knowledge, dated Feb. 2003, 1 page.*
"Astaxanthin Mechanism of Action" 1 page, downloaded from www.transferpoint.com/Articles.*
Jones N. W., California State Journal of Medicine, vol. VII, No. 2, pp. 56-59, Feb. 1909.*
Peptic Ulcer Disease, downloaded from www.dubuqueinternalmed.com/pamphlets/pepticulcer.html, Jan. 2001, 4 pages.*
Young et al. J. Am Geriatr. Soc., Jan. 1980, vol. 28(1), pp. 46-47, abstract.*
"Agaricus extract", downloaded from www.literatureresearch.net, dated 1999, 2 pages.*
Hywood et al. "A Bowel Flora Protocol for Dybiosis Management", No. 41, Jul. 2004, pp. 1-6, downloaded from www.mediherb.com.*
Yamakoshi et al. Microbial Ecology in Health and Disease 2001; vol. 13 pp. 25-31.*
Baidoo Feeding Strategies for Manipulating Manure Content, downloaded from www.mb.cadated Jan. 2001, 10 pages.*
La Manna et al. Dept of Ani Sci, OSU, 1998, "Effects of Agrado™, an Antioxidant, on Odor of Cattle Feces", pp. 69-71.*
Lorenz, Todd. "Astaxanthin, Nature's Super Carotenoid", BioAstin ™ Technical Bulletin #062, Cyanotech Corporation, dated Oct. 2000, 19 pages.*

* cited by examiner

*Primary Examiner* — Chhaya Sayala
(74) *Attorney, Agent, or Firm* — Seager, Tufte & Wickhem LLC

(57) ABSTRACT

There is provided pet food comprising astaxanthin and/or an ester thereof as an active component and having an effect of deodorizing excrement such as urine and feces, effects of improving sleep, sensibility such as perception and cognition, and visual sense, and an effect of treating, improving or preventing diabetes and diabetic complications. The pet food can deodorize excrement such as urine and feces, improve sleep, sensibility such as perception and cognition, and visual sense, and treat, improve or prevent diabetes and diabetic complications.

4 Claims, No Drawings

ASTAXANTHIN-CONTAINING PET FOODS

RELATED APPLICATIONS

This application is a continuation of U.S. application Ser. No. 10/583,482 filed Sep. 29, 2006, now abandoned, which is a 371 application of PCT/JP04/18950 filed Dec. 17, 2004, which claims priority to JP 2003-422304 filed Dec. 19, 2003.

TECHNICAL FIELD

The present invention relates to pet food containing astaxanthin and/or an ester thereof and having an effect of deodorizing excrement such as urine and feces, effects of improving sleep, sensibility such as perception and cognition, and visual sense, and an effect of treating, improving or preventing diabetes and diabetic complications for use in pets such as a mouse, rat, guinea pig, rabbit, monkey, dog, cat, hamster, pig, cow, sheep, horse, crocodile, alligator, snake, lizard, and bird.

BACKGROUND ART

Astaxanthin is a kind of carotenoid like β-caretinoid, and is a red pigment present in a wide variety of edible creatures living in the nature, particularly, in the ocean, including shellfishes such as shrimp and crab, fishes such as sermon and sea-bream, algae such as green algae *Haematococcus*, and yeasts such as red yeast *Phaffia*.

It has been recently found that astaxanthin has a strong antioxidative action, which is 100 to 1,000 times as high as vitamin E (α-tocopherol) and about 40 times as high as β-carotene. Astaxanthin, which has been conventionally treated merely as a pigment, but is now expected as healthy foodstuff. Many reports inform that astaxanthin has other actions besides the actions mentioned above, for example, anti-inflammatory action, anti-arteriosclerotic action, anti-diabetic action, protecting action of the retina against light damage, circadian rhythm control action, immunopotentiation action, anti-stress action, action of improving muscular endurance, action of improving sperm quality, and action of suppressing induction of bladder cancer. It is also reported that astaxanthin is effective for the skin since it has an action of suppressing pigment deposition, melanogenesis, and optical aging.

Recently, with growing interest in pets, in particular, growing number of indoor pets, health, appearance and behavior of pets have caused problems that affect the owners. The problems, which are particularly caused by environments and feeding conditions of pets, include sleep disorder, deterioration of sensibility such as perception and cognition and visual sense, odor emitted from excrement such as feces and urine, and symptoms of diseases such as diabetes and diabetic complications. These symptoms and conditions of pets have been controlled by medication. However, the symptoms and conditions are chronic and side effect caused by medication is a matter of concern. For these reasons, it has been desired to develop a something derived from a nontoxic substance, that is, naturally occurring substance, having a therapeutic/preventive/improvement effect on the symptoms and conditions. Up to present, astaxanthin and/or an ester thereof has not yet been known to have effects of deodorizing excrement such as urine and feces, improving sleep, sensibility such as perception and cognition and visual sense, and an effect of treating, improving or preventing diabetes and diabetic complications of pets.

Recently, with growing number of singles, elderly persons and nuclear families in our country, the number of families having a pet as well as the number of indoor pets are increasing. In the circumstance, odor emitted from excrement such as feces and urine is a problem for owners. Odor complaints, which have been mostly directed to odor of apartment houses and family-owned houses, now increasingly directed to urban life. In these circumstances, it has been strongly desired to develop pet food safe and effective in deodorizing excrement.

As examples of pet food effective in deodorizing excrement, there are a fermented healthy feed containing a solution of a fermented product by *Bacillus subtilis* and a tree extract (see Patent Document 1); a fecal odor deodorant for domestic animals containing a copper chlorophyllin salt as an active ingredient (see Patent Document 2); a feed effective in deodorizing animal excrement containing an extract from cinnamon leaves with a water/methanol mixture solution (see Patent Document 3); and a composition for deodorizing excrement containing a type of *lactobacillus* and a tea extract (see Patent Document 4).

By virtue of advance in medical technology and improvement of indoor conditions, the life time of pets is extended. With the increase of the lifetime, aging of pets comes to be a matter of concern. In addition, the circadian rhythm of pets is frequently disturbed by people's activity, that is, keeping late and irregular hours, with the result that the pets increasingly suffer from a sleep disorder. The sleep disorder of a pet not only damages pet's health but also disturbs owner's good sleep since the pet and the owner have different life patterns (rhythm of life).

As pet food effective in improving sleep, mention may be made of a composition constituted of tryptophan and a carbohydrate, for facilitating animal sleep (see Patent Document 5); a pharmaceutical composition containing a novel melatonin derivative as an active ingredient, for treating a mammalian sleep disorder (see Patent Document 6); and a pharmaceutical composition containing an acetylcholinesterase inhibitor, for treating an age-related behavior disorder of a pet animal (see Patent Document 7).

When the sensibility of a pet such as perception and olfactory deteriorate with aging, diseases, or a disorder of rhythm of life by urbanization of living environment, the pet is known to become no longer adorable. Patent Document 7 teaches that an acetylcholinesterase inhibitor is administered to improve the sensibility of a pet.

To improve the visual sense of a pet, a method of using astaxanthin and/or an ester thereof to treat retinopathy is known (see Patent Document 8) and an eye control improver containing astaxanthin and/or an ester thereof is known (see Patent Document 9). Furthermore, it has been reported that a food or drink containing astaxanthin and/or an edible ester thereof, for preventing cataract or suppressing progress thereof, is capable of suppressing not only onset of cataract or suppressing progress thereof but also disorders such as monocular diplopia, eye fatigue, and halation, associated with visual disorder due to cataract (see Patent Document 10).

The number of pets suffering from diabetes has been increased by the reasons that the number of pets increases, the living environment of a pet changes, and excessive food is given by the owner of lack of knowledge. Diabetes is mostly developed by a genetic reason. Besides this, diabetes is triggered by an elevated blood glucose level, which is caused by excessive feeding and living habits of indoor life, shortage of exercise, and accompanies various types of complications. It is difficult to limit the amount of a meal in view of the eating habit of a pet as well as to inject insulin to the pet. Administration of medicament may cause harmful effects in various ways. In these circumstances, it is desired to develop food containing a naturally occurring nontoxic substance for treating, improving or preventing diabetes and diabetic complications.

[Patent Document 1] Japanese Laid-Open Patent Publication No. 5-192087

[Patent Document 2] Japanese Laid-Open Patent Publication No. 3-266943

[Patent Document 3] Japanese Laid-Open Patent Publication No. 2001-258480

[Patent Document 4] Japanese Laid-Open Patent Publication No. 2002-114690

[Patent Document 5] Japanese Laid-Open Patent Publication No. 58-201715

[Patent Document 6] Japanese Laid-Open Patent Publication No. 7-196493

[Patent Document 7] Japanese Laid-Open Patent Publication No. 2000-309545

[Patent Document 8] U.S. Pat. No. 5,527,533

[Patent Document 9] International Publication WO 02/094253

[Patent Document 10] Japanese Laid-Open Patent Publication No. 10-276721

DISCLOSURE OF THE INVENTION

An objective of the present invention is to provide pet food having an effect of deodorizing excrement such as urine and feces, effects of improving sleep, sensibility, and visual sense, and an effect of treating, improving or preventing diabetes and diabetic complications, for use in pets such as a mouse, rat, guinea pig, rabbit, monkey, dog, cat, hamster, pig, cow, sheep, horse, crocodile, alligator, snake, lizard, and bird.

The present inventors have conducted studies to achieve the aforementioned objective. As a result, the inventors have found that astaxanthin and/or an ester thereof has an effect of deodorizing excrement such as urine and feces, effects of improving sleep, sensibility, and visual sense, and an effect of treating, improving or preventing diabetes and diabetic complications and achieved the present invention. The present invention is attained based on the finding mentioned above.

To describe more specifically, the present invention provides:

(1) Pet food characterized by comprising astaxanthin and/or an ester thereof;

(2) The pet food according to item (1), characterized by comprising astaxanthin and/or an ester thereof and having an effect of deodorizing excrement;

(3) The pet food according to item (1), characterized by comprising astaxanthin and/or an ester thereof and having an effect of improving sleep;

(4) The pet food according to item (1), characterized by comprising astaxanthin and/or an ester thereof and having an effect of improving sensibility;

(5) The pet food according to item (1), characterized by comprising astaxanthin and/or an ester thereof and having an effect of improving visual sense;

(6) The pet food according to item (1), characterized by comprising astaxanthin and/or an ester thereof and having an effect of treating, improving or preventing diabetes and diabetic complications;

(7) The pet food according to items (1) to (6), characterized in that the pet is at least one selected from the group consisting of a mouse, rat, guinea pig, rabbit, monkey, dog, cat, hamster, pig, cow, sheep, horse, crocodile, alligator, snake, lizard, and bird; and (8) The pet food according to items (1) to (6), characterized in that the pet is a dog and/or a cat.

BEST MODE FOR CARRYING OUT THE INVENTION

By feeding a pet with the pet food according to the present invention containing nontoxic astaxanthin, odor from pet excrement can be reduced and sensibility of a pet can be improved to enable the pet to quickly respond to a person. In addition, the pet can sleep well, with the result that health conditions are improved. Further, visual sense is improved and diabetes and diabetic complications can be treated, improved and prevented. Thus, a pet can be reared more satisfactorily.

The "astaxanthin" used herein refers to naturally occurring astaxanthin or synthetic astaxanthin. The naturally occurring astaxanthin can be obtained from, for example, a crust, egg and organ of shellfishes such as shrimp, krill and crab, the skin and egg of various types of fish, algae such as green algae *Haematococcus*, yeasts such as red yeast *Phaffia*, marine bacteria, and seed plants such as an *Amur adonis* and buttercup. Extracts of astaxanthin from a natural substance and chemically synthesized astaxanthin are commercially available and thus easily obtained.

Astaxanthin can be obtained by culturing red yeast *Phaffia*, green algae *Haematococcus*, and marine bacteria, etc. in an appropriate medium in accordance with a known method. Of them, green algae *Haematococcus* is most suitably used since it is easily cultured and extracted, contains astaxanthin in the highest concentration, and productivity of astaxanthin is high. To obtain green algae *Haematococcus* having a high content of astaxanthin, it is preferably cultured in an airtight chamber having no heterologous micro organism included and proliferated and rarely containing foreign substances, for example, suitably cultured in an airtight dome, conical or cylindrical culture apparatus by use of a culture medium having a gas supply device movable within the apparatus (see the pamphlet of International Publication WO 99/50384); in an airtight culture apparatus while applying light from a light source placed within the apparatus; or in a flat-plate culture vessel.

For extracting and purifying astaxanthin from the cultured product or shellfish, various methods are known. Since a diester of astaxanthin is soluble in oil, a component containing astaxanthin can be extracted with oil-soluble organic solvent, such as acetone, alcohol, ethyl acetate, benzene and chloroform from a natural substance containing astaxanthin. After the extraction, the solvent is removed in accordance with a customary method to obtain a concentrated mixture of a monoester of astaxanthin and a diester of astaxanthin. If desired, the resultant concentrated mixture may be further purified.

As astaxanthin, use may be made of an astaxanthin extract obtained as mentioned above, a powder and an aqueous solution containing the astaxanthin extract, or dried products of red yeast *Phaffia*, green algae *Haematococcus*, and marine bacteria, and pulverized products thereof.

Astaxanthin is 3,3'-dihydroxy-$\beta,\beta$-carotene-4,4'-dione and has stereoisomers. As the stereoisomers, mention may be made of three types of stereoisomers, (3R,3'R)-astaxanthin, (3R,3'S)-astaxanthin, and (3S,3'S)-astaxanthin. Any one of the aforementioned astaxanthin stereoisomers may be employed in the present invention.

In the description of the present invention, unless otherwise specified, astaxanthin and/or an ester thereof is included in astaxanthin according to the present invention. As an ester of astaxanthin, a monoester and/or a diester of astaxanthin is included.

It is known that astaxanthin is a highly safe compound since no mutagenicity is observed.

In pet food containing astaxanthin as an active ingredient according to the present invention, use may be made of at least one type of astaxanthin selected from the group consisting of free astaxanthin, a monoester and a diester of astaxanthin. The diester of astaxanthin, since it has two hydroxyl groups protected by ester bonds, has a higher stability than free astaxanthin and a monoester of astaxanthin, so that it rarely decomposed by oxygen. However, once it is taken into a living body, the diester of astaxanthin is rapidly hydrolyzed by biological enzyme into astaxanthin to exert the effect.

As the monoester of astaxanthin, mention may be made of esters obtained by esterification with a lower or higher saturated fatty acid, or lower or higher unsaturated fatty acid. Specific examples of such a lower or higher saturated fatty acid, or lower or higher unsaturated fatty acid may include acetic acid, lauric acid, myristic acid, pentadecanoic acid, palmitic acid, palmitoleic acid, heptadecanoic acid, elaidic acid, ricinoleic acid, petroselinic acid, vaccenic acid, eleostearic acid, punicinic acid, licanoic acid, palynalic acid, gadolic acid, 5-eicosenoic acid, 5-docosenoic acid, cetolic acid, ercinoic acid, 5,13-docosadienoic acid, selacholic acid, decenoic acid, steric acid, dodecenoic acid, oleic acid, stearic acid, eicosapentaenoic acid, docosahexaenoic acid, linoleic acid, linolenic acid, and arachidonic acid. Diesters of astaxanthin may include diesters obtained by esterification with the same or different fatty acids selected from the aforementioned fatty acids.

Examples of astaxanthin monoesters further may include monoesters obtained by esterification with an amino acid such as glycine and alanine; a mono- or poly-carboxylic acid such as acetic acid and citric acid; an inorganic acid such as phosphoric acid and sulfuric acid; a saccharide such as glucoside; a glyco-fatty acid such as glycoglycero-fatty acid and glycosphingo-fatty acid; and a fatty acid such as glycero-fatty acid; and glycerophosphoric acid. Note that, if considerable, salts of the monoesters mentioned above may be included.

Examples of the diesters of astaxanthin may include diesters obtained by esterification with the same or different acids selected from the group consisting of the aforementioned lower saturated fatty acids, higher saturated fatty acids, lower unsaturated fatty acids, higher unsaturated fatty acids, amino acids, mono- or poly-carboxylic acids, inorganic acids, saccharides, glycol-fatty acids, fatty acids and glycerophosphoric acid. Note that, if considerable, salts of the aforementioned diesters may be included.

Examples of diesters of glycerophosphoric acid may include saturated fatty acid esters of glycerophosphoric acid or esters of glycerophosphoric acid including fatty acids selected from higher unsaturated fatty acids, unsaturated fatty acids and saturated fatty acids.

To improve the effect of astaxanthin contained in the pet food according to the present invention, not less than one type of antioxidant may be added. Examples of such antioxidant include vitamin E (tocopherol), vitamin C, carotenoid, polyphenol, oil containing unsaturated fatty acid and natural extracts.

Vitamin E includes vitamin E, tocotrienol, and derivatives thereof. Also, as vitamin E, use may be made of oil containing not less than one type of them. Specific examples of vitamin E include dl-α-tocopherol, d-α-tocopherol, dl-α-tocopherol acetate, d-α-tocopherol acetate, dl-α-tocopherol succinate, d-α-tocopherol succinate, dl-α-tocopherol nicotinate, and d-α-tocopherol nicotinate; dl-β-tocopherol, d-β-tocopherol, dl-β-tocopherol acetate, d-β-tocopherol acetate, dl-β-tocopherol succinate, d-β-tocopherol succinate, dl-β-tocopherol nicotinate, and d-β-tocopherol nicotinate; dl-γ-tocopherol, d-γ-tocopherol, dl-γ-tocopherol acetate, d-γ-tocopherol acetate, dl-γ-tocopherol succinate, d-γ-tocopherol succinate, dl-γ-tocopherol nicotinate, and d-γ-tocopherol nicotinate; d-δ-tocopherol, d-δ-tocopherol, dl-δ-tocopherol acetate, d-δ-tocopherol acetate, dl-δ-tocopherol succinate, d-δ-tocopherol succinate, dl-δ-tocopherol nicotinate, and d-δ-tocopherol nicotinate; α-tocotrienol; β-tocotrienol; γ-tocotrienol; and δ-tocotrienol. Of them, dl-α-tocopherol, dl-α-tocopherol acetate, dl-α-tocopherol succinate, dl-α-tocopherol nicotinate, α-tocotrienol, β-tocotrienol, and γ-tocotrienol are particularly preferable.

Vitamin C includes vitamin C and derivatives thereof. Examples of the vitamin C derivatives may include glycosides such as glucoside ascorbate; alkyl esters of L-ascorbic acid such as L-ascorbyl palmitate, L-ascorbyl isopalmitate, L-ascorbyl dipalmitate, L-ascorbyl diisopalmitate, L-ascorbyl stearate, L-ascorbyl isostearate, L-ascorbyl distearate, L-ascorbyl diisostearate, L-ascorbyl myristate, L-ascorbyl isomyristate, L-ascorbyl dimyristate, L-ascorbyl diisomyristate, L-ascorbyl 2-ethylhexanoate, L-ascorbyl di-2-ethylhexanoate, L-ascorbyl oleate, L-ascorbyl dioleate, ascorbyl tetrahexyldecanoate, and ascorbyl tetraisopalmitate; phosphoric esters of L-ascorbic acid such as L-ascorbyl-2-phosphate, and L-ascorbyl-3-phosphate; and sulfuric esters of L-ascorbic acid such as L-ascorbyl-2-sulfate, and L-ascorbyl-3-sulfate.

Examples of the carotenoid include β-carotene, α-carotene, lycopene, lutein, canthaxanthin, astaxanthin, zeaxanthin, β-apo-8'-carotinal, carotene derived from Donariera, carrot and palm oil, and tomato pigment.

Examples of the oil containing unsaturated fatty acid may include oils containing unsaturated fatty acid such as linoleic acid, arachidonic acid, α-linolenic acid, eicosapentaenoic acid, and docosahexaenoic acid; glyceroids containing these unsaturated fatty acids; and phospholipids containing these unsaturated fatty acids. Specific examples are sardine oil, perilla oil, kiwifruit seed oil, camellia oil, pigeon wheat oil, grape seed oil, black currant oil, Borage seed oil, evening primrose oil, hemp oil, corn oil, soybean oil, linseed oil, butter, lard, coconut oil, palm oil, olive oil, canola coil, olein-rich safflower oil, and fish oil.

Examples of the natural extracts include *eleutherococcus* extract, kiwi extract, *Sophora angustifolia* extract, *Millettia reticulate* extract, *Rhodiola Rosea* extract, coffee extract, wheat extract, *Asarum Sieboldi* extract, *Paeonia lactiflora* extract, *Inula britannica* extract, evening primrose extract, tomato extract, grape extract, black currant extract, garden balsam extract, *melothria heterophylla* extract, *coix* extract, *Althaea* extract, *Polygonum Bistorta* root extract, Nettle Extract, *Artemisia Capillaris* flower extract, turmeric extract, *Coptis* extract, seaweed extract, *Gentiana* extract, *Scutellaria baicalensis* extract, *Symphytum officinale* extract, *Perilla* extract, *Lonicera Japonica* Extract, clove extract, white kidney bean extract, *Angelica acutiloba* Kitagawa extract, *Saxifraga Sarmentosa* extract, Rosemary extract, *Sanguisorba officinalis* extract, *Ginkgo* tree leaf extract, and blue berry extract.

In the pet food according to the present invention, the ratio of the antioxidant to astaxanthin varies depending upon the types of astaxanthin and antioxidant to be blended; however, the ratio of the antioxidant to astaxanthin is generally 0.1 to 200 parts by weight, preferably 0.2 to 20 parts by weight, and more preferably 0.5 to 5 parts by weight based on 1 part by weight of astaxanthin.

Pet food containing astaxanthin according to the present invention can be used for exerting effects of deodorizing excrement, and improving sleep, sensibility and visual sense, and treating, improving or preventing diabetes and diabetic complications of a pet.

The effect of deodorizing excrement used herein refers to reducing, removing and preventing odor from pet excrement, and more specifically, means that bad odor of pet excrement is drastically reduced by feeding pet food containing astaxanthin. It is considered that astaxanthin inhibits enteric bacteria and urease derived from a plant, which decompose urea and are responsible for generating ammonia that is a main cause of bad odor, and controls the enteral conditions, thereby accelerating growth of useful bacteria in the intestine.

The effect of improving sleep of a pet used herein refers to an effect for improving, treating, and suppressing a sleep disorder caused by stress, disease, change in the rhythm of life, medication, physical disorder, and aging. The sleep disorder refers to insomnia such as disturbance of sleep induction, and disturbance of sound sleep. The symptom of the disturbance of sleep induction means difficulty with falling asleep. The symptoms of the disturbance of sound sleep include "night awakening", which is a sleep disorder involving awakening from sleep several times in the midnight and feeling of insufficient sleep; "early awakening", which is a sleep disorder involving awakening at dawn and cannot get back to sleep to the morning; and "lack of feeling of sufficient sleep", which is a sleep disorder involving no sense of sufficient sleep despite the sufficient time of sleep.

The effect of improving sensibility of a pet used herein refers to improving, treating and suppressing disorder in perception and cognition ability caused by stress, disease, change in the rhythm of life, and aging. To be more specific, when sensibility is improved, a pet responds sensitively to sound and a stranger, expresses emotion such as delight, when the pet owner attracts attention by behavior and gives food. Furthermore, a pet frequently tries to draw owner's attention and becomes willing to greet to the owner. Since a pet is improved in health conditions, the hair condition of the pet improves.

The effect of improving visual sense of a pet used herein refers to improving, treating or suppressing a disorder of visual sense caused by stress, disease, change in the rhythm of life, and aging. Examples of the disorder of visual sense include refractive error and adjustment error of the eye such as near sight, far sight, distorted visual sense and old sight, diseases such as retinopathy, maculopathy, glaucoma, cataract, dry eye, and conjunctivitis, and fatigue. Also, effect of preventing eye mucus is included.

The effect of treating, improving or preventing diabetes of a pet used herein refers to treating, improving or preventing diabetes and diabetic complications developed as the result that a blood glucose level increases due to living habits such as excessive feeding and shortage of exercise caused by indoor life, besides a genetic reason. The present invention is effective against both type I and type II diabetes, and more effective against type II diabetes. Insulin resistance, which is acquired characteristic of type II diabetes, is frequently associated with obesity, in particular, accumulation of visceral fat. Also, hyperlipemia and high blood pressure are frequently complicated with type II diabetes. The pet food according to the present invention improves the symptom of a high blood glucose level by reducing an elevated blood glucose level, thereby treating, improving or preventing diabetes.

The pet food according to the present invention has an effect of treating, improving, or preventing diabetic complications such as nervous disorder, retinopathy, nephropathy, and ischemia by treating, improving, or preventing diabetes. The pet food is effective in treating, improving or preventing the nervous disorders such as sudden deafness, abnormality in eye and face (paralysis and pain), postural hypotension, diarrhea, constipation (digestive symptom), urinary disturbance, appendicular pain, perceptional abnormality, muscular atrophy, and necropathy. The pet food is also effective in treating, improving or preventing retinopathy such as macular degeneration, glaucoma, cataract, simple retinopathy, pre-proliferative retinopathy, and proliferative retinopathy. The pet food is also effective in treating, improving or preventing ischemia such as brain infarction and myocardial infarction.

The form and state of the pet food according to the present invention is not particularly limited. The pet food may be a solid preparation, solid, pellet, granule, biscuit, and paste and may be dry, semidry (for example, the moisture content of pet food is 10 to 50 wt %), or wet (for example, canned pet food having a moisture content of 50 to 80 wt %). The pet food of the present invention may be produced by adding and blending astaxanthin with a commercially available material for pet food or spraying an aqueous solution of astaxanthin to a commercially available pet food in an appropriate production step thereof. Also, the pet food of the present invention may be produced by adding and blending astaxanthin with a commercially available pet food or spraying astaxanthin on such pet food. Alternatively, the pet food may be produced in the form of an easy-to-take solid preparation such as an oral tablet, sublingual tablet, pill, powder, dusting powder, subtle granule, granule, capsule and soft capsule, in the same manner as in a dietary supplement for a human.

As a raw material that can be blended in pet food, any material may be used as long as it can be used in pet food. As a raw material for pet food, any material used in the art may be used and include animal materials such as fish flour, fish meat, seafood, fishmeal, animal meat, meat meal, meat and bone meal, blood meal, feather meal, silkworm pupa oil cake, skim milk, animal fat and oil (such as bovine oil, swine oil, bone oil), hen egg, and milk; micro organisms such as beer yeast and torula yeast; cereals such as corn, milo, wheat, barley, rye, oat, wheat powder, brown rice, blister, soybean, ground soybean, and cassaya; starch such as α-starch and potato starch; oil cakes such as soybean oil cake, molt soybean oil, rapeseed oil cake, peanut oil cake, palm oil cake, sunflower oil cake, linseed oil cake, sesame oil cake, safflower oil cake, palm kernel oil cake, and kapoc oil cake; bran such as rice bran, barley bran, and wheat bran; fabrication waste such as gluten feed, gluten meal, starch pulp, molasses, soy source cake, beer pulp, beet pulp, bagasse, bean curd refuse, malt root, orange peel, and orange juice pulp; cellulose such as alfalfa meal, timothy hay, and straw; and other ingredients such as excipients, binders, disintegrators, salts, saccharides such as sugar, vitamins, amino acids, and minerals. These may be used singly or in a combination of two or more types depending upon the type of pet.

As a raw material to be used in the solid preparation, mention may be made the aforementioned materials, and carriers generally used in human food. The solid preparation can be produced by blending such a carrier and astaxanthin homogeneously. Examples of such a carrier include saccharides such as sucrose, sorbitol and fructose; glycols such as polyethylene glycol and propylene glycol; oils such as sesame oil, rapeseed oil, olive oil and soybean oil; and flavors such as strawberry flavor and peppermint flavor. In the case where the solid preparation is a powder, pill, capsule, soft capsule and tablet, use may be made of an excipient such as lactose, glucose, sucrose, lactose, mannitol, cornstarch, and silicon dioxide; a disintegrator such as starch and sodium alginate; a lubricant such as magnesium stearate and talc; a binder such as polyvinyl alcohol, hydroxypropyl cellulose, gelatin and casein; an emulsifier such as glycerin fatty acid ester, sucrose fatty acid ester, sorbitan fatty acid ester, saponin, and lecithin; a thickener such as guar gum, alginic acid, carageenan, agar, pectin, arabia gum, crystalline cellulose; and a plasticizer such as glycerin. Tablets and soft capsules are preferable since they are easily taken.

If necessary, the pet food may contain additives such as a toughening agent, quality improver, antibiotics, antibacterial agent, enzyme, antifungal agent, antioxidant, coloring agent, sweetener, and flavor.

The content of astaxanthin in pet food is not particularly limited and may be selected within the palatability range, for example, from 0.0001 to 10 wt %, preferably 0.0005 to 5 wt %, and further preferably 0.0005 to 3 wt % in terms of free astaxanthin based on the total amount of pet food.

A solid preparation is suitable since a dose per time or day can be determined. The content of astaxanthin per solid preparation of 200 to 1000 mg in weight is 0.1 to 10 mg, and preferably 0.2 to 5 mg in terms of free astaxanthin.

The dose of pet food given to a pet can be selected depending upon the age and weight of the pet, for example, 1 to 500, preferably 2 to 300, and further preferably, 5 to 200 μg/day in terms of free astaxanthin per kilogram of the weight of the pet. Note that the pet food can be given at any time and may be given once or a plurality of times in a day.

The present invention may be applied to various types of pets. Pets are animals improved by a human not for food but for a companion animal and have many chances to contact with a human. Examples of pets include a mouse, rat, guinea pig, rabbit, monkey, dog, cat, hamster, pig, cow, sheep, horse, crocodile, alligator, snake, lizard, and bird. The present invention is preferably applied to particularly dogs and cats.

The present invention will be explained by way of the following Examples, which may not be construed as limiting the present invention. The astaxanthin used in Examples below is astaxanthin oil containing an extract from algae *Haematococcus* and manufactured by Fuji Chemical Industry Co., Ltd. AstaReal 50F (trade name, manufactured by Fuji Chemical Industry Co., Ltd.) used in Examples below is oil containing a fatty acid ester of astaxanthin (containing 5% astaxanthin in terms of free astaxanthin) and triglycerides. AstaReal powder (trade name, manufactured by Fuji Chemical Industry Co., Ltd.) is a powder product containing AstaReal 50F in a content of 20%.

EXAMPLE 1

Twenty nine dogs (2.2 to 27 kg in weight) each were fed with not a special meal but commercially available dog food for a month. During the following month, they were fed with the same commercially available dog food and tablets containing astaxanthin in an amount of 1 mg in terms of free astaxanthin and manufactured by Menione. A meal was given twice a day and a single tablet containing astaxanthin was given per meal.

After one month of administration, the dogs were evaluated for the degree of deep sleep during night, sensibility to stimulation externally applied, and visual sense in comparison with those before the administration. The results are shown in Table 1.

TABLE 1

| Evaluation items | Evaluation results (number of dogs) | | |
| --- | --- | --- | --- |
| | Improved | No change | Deteriorated |
| Deep sleep | 8 | 21 | 0 |
| Sensibility | 12 | 17 | 0 |
| Visual sense | 10 | 19 | 0 |

When a dog got sleep well and showed a quick response to abnormal sound during sleep, the deep sleep was evaluated as "improved". When a dog came to aggressively run around, showed expressive face, and had hair gloss improved, the sensibility was evaluated as "improved". When a dog showed a change in attitude, for example, a dog focused his eye at the owner or an object and the amount of eye mucus reduced, the visual sense was evaluated as "improved". The numerical values in the column entitled "Evaluation results" of Table 1 represent the number of dogs corresponding to each item. As is apparent from the results of Table 1, deep sleep, sensibility and visual sense all were improved.

EXAMPLE 2

Eight cats (5.8 to 8 kg in weight) each were fed with tablets containing astaxanthin in an amount of 1 mg in terms of free astaxanthin, manufactured by Menione for a month, in the same manner as in Example 1.

After one month of administration, the cats were evaluated for the degree of deep sleep during night, sensibility to stimulation externally applied, and visual sense in comparison with those before the administration. The results are shown in Table 2.

TABLE 2

| Evaluation items | Evaluation results (number of cats) | | |
| --- | --- | --- | --- |
| | Improved | No change | Deteriorated |
| Deep sleep | 5 | 3 | 0 |
| Sensibility | 2 | 6 | 0 |
| Visual sense | 2 | 6 | 0 |

As is apparent from the results shown in Table 2, deep sleep, sensibility and visual sense all were improved.

EXAMPLE 3

Effect of Improving Feces Odor

Four dogs were fed only with the same commercially available dog food for 3 months or more, and thereafter, two AstaReal tablets (manufactured by Natureal Corporation, containing 0.67 mg of free astaxanthin per tablet in terms of free astaxanthin) per day were given to the dogs at dinner for 4 weeks. The dogs were confirmed to keep in healthy conditions without exhibiting diarrhea and fatigue before and during the administration of astaxanthin. The feces discharged before and after administration of astaxanthin were collected. Samples were prepared each by taking a piece from the top portion, middle portion and end portion in the same amount and mixing these pieces. The samples were placed in a shielded vessel of 100 ml in volume and kept in dark and used in tests within 24 hours.

[Feces Odor Test]

Odor of the samples was measured by an odor tester (KAL-MOR-Σ, manufactured by Kalmor Co.) in a room maintained at 22° C. To explain more specifically, the odor of an airtight vinyl bag of 280 mm×200 mm containing no sample was measured as an initial value by inserting a test probe. Then, 100 mg of sample was weighed, placed in the vinyl bag and stand still for 15 minutes. The odor of the vinyl bag having the sample placed therein was measured (measured value). The value of the odor was obtained by subtracting the initial value from the measured value.

TABLE 3

Change in odor value

| Sex | Weight (kg) | Odor values | | |
| --- | --- | --- | --- | --- |
| | | Before administration | 4 weeks after administration | Reduced value |
| Male | 17 | 448 | 261 | 187 |
| Female | 10 | 220 | 137 | 83 |
| Female | 14 | 470 | 44 | 426 |
| Female | 7 | 455 | 179 | 276 |
| Average | | 398.3 | 155.3 | 243.0 |

The results shown in Table 3 were obtained at not more than 5% level of significance. Thus, the results are statistically significant. As is apparent from the results shown in Table 3, odor of the excrement clearly is decreased by administrating astaxanthin.

EXAMPLE 4

A beagle dog (about 10 kg in weight, 6 months old) was prepared as a diabetic model by administering streptozotocin (STZ) purchased from Sankyo Laboratories. The beagle dog was fed with food containing AstaReal 50F (manufactured by Fuji Chemical Industry Co., Ltd. and containing 0.67 mg of astaxanthin (in terms of free astaxanthin) per tablet (300 mg) for 4 weeks. Blood was taken from the dog at the initiation time, 2 weeks after, and 4 weeks after the test. The blood serum was separated from each of the samples and blood glucose level of the serum was measured. The beagle dog was housed in a metal cage and raised under the conditions: temperature of 22±2° C., humidity 55±10%, and light exposure: 12 hours (7 a.m. to 7 p.m.). AstaReal 50F (1 g) was given to the dog together with food every day, 9 a.m.

TABLE 4

Change in blood glucose level (mg/dL)

| Before administration | 2 weeks after administration | 4 weeks after administration |
| --- | --- | --- |
| 413.2 | 273.5 | 257.3 |

As is apparent from Table 4, the blood glucose level in the diabetic beagle dog decreased 2 weeks and 4 weeks after administration with statistical significance.

EXAMPLE 5

Astaxanthin was administered to a beagle dog by feeding it with food containing AstaReal 50 F for 4 weeks. Difference between before and after administration was observed. The beagle dog (about 10 kg in weight, 6 months old) was purchased from Sankyo Laboratories. After the purchase, preparatory feeding for about 4 weeks was performed to confirm that the dog had no abnormal conditions, weight and feed amount. The beagle dog having no abnormality was housed in a metal cage and raised under the conditions: temperature of 22±2° C., humidity 55±10%, and light exposure: 12 hours (7 a.m. to 7 p.m.). AstaReal 50F (1 g) was given to the dog together with food every day, 9 a.m.

After administration of astaxanthin, the odor of excrement such as feces and urine, sensibility to stimuli externally applied, degree of deep sleep during night, and visual sense were observed as to whether they are improved or not. The results are shown in Table 5.

TABLE 5

| Evaluation items | Evaluation results |
| --- | --- |
| Deodorant of excrement | + |
| Increase of deep sleep | + |
| Increase of sensibility | + |
| Improvement of visual sense | + |

A reference symbol + in the column entitled "Evaluation results" in Table 5 shows that improvement effect was obtained. From the results of Table 5, it is apparent that pet food containing astaxanthin according to the present invention is effective in improving deodorant of excrement, deep sleep, sensibility and visual sense.

EXAMPLE 6

| AstaReal powder | 10 parts by weight |
| --- | --- |
| Blue berry powder | 2 parts by weight |
| V premix | 3 parts by weight |
| Lactose | 50 parts by weight |
| Potato starch | 32 parts by weight |
| Polyvinyl alcohol | 2 parts by weight |
| Magnesium stearate | 1 part by weight |

The components listed above were blended by a V-type mixer and made into tablets by a rotary tablet machine (HT-AP18SS-II, manufactured Hata Iron Works Co., Ltd.) to produce tablet-form pet food.

EXAMPLE 7

| Wheat powder | 34.9 parts by weight |
| --- | --- |
| Starch | 23 parts by weight |
| Dried pulverized fish meal | 15 parts by weight |
| Dried meat and bone meal | 15 parts by weight |
| Skim milk | 5 parts by weight |
| Sucrose ester | 3 parts by weight |
| Animal fat and oil | 2 parts by weight |
| Vitamins/minerals | 1 part by weight |
| AstaReal 50F | 0.1 part by weight |
| Water | 55 parts by weight |

The components listed above were blended and made into pellets of 100 to 300 mg having a size of 4 mm ωxabout 5 to 10 mm) by a disk-pellet pelletizer manufactured by Fuji Paudal Co. Ltd. The pellets were dried at 50° C. for 10 hours to obtain dry food.

EXAMPLE 8

| Corn | 33 parts by weight |
|---|---|
| Wheat | 30 parts by weight |
| Defatted soybean | 14.9 parts by weight |
| Meat meal | 10 parts by weight |
| Chicken meal | 5 parts by weight |
| Wheat bran | 5 parts by weight |
| Vitamin/mineral mix | 1 part by weight |
| AstaReal 50F | 0.1 part by weight |

The components listed above were blended, pulverized, and classified through a sieve having openings of 1 mm. Water was added to the resultant mixture to contain about 27 wt % of a solid matter. The mixture was extruded by a cooking extruder (manufactured by Wenger Manufacturing, Inc.) equipped with round dies of 8 mm in diameter to obtain a swollen product. The swollen product thus obtained was dried by a belt-type dryer at 120° C. for 20 minutes and soybean oil (5 parts by weight) was sprayed onto the swollen product (95 parts by weight) to obtain dry dog food.

EXAMPLE 9

| Corn | 32.9 parts by weight |
|---|---|
| Wheat powder | 25 parts by weight |
| Defatted soybean | 15 parts by weight |
| Fish meal | 10 parts by weight |
| Meat meal | 10 parts by weight |
| Chicken meal | 5 parts by weight |
| Vitamin/mineral mix | 1 part by weight |
| Calcium phosphate | 1 part by weight |
| AstaReal 50F | 0.1 part by weight |

The components listed above were blended, pulverized, and classified through a sieve having openings of 1 mm. Water was added to the resultant mixture to contain about 27 wt % of a solid matter. The mixture was extruded by a cooking extruder (manufactured by Wenger Manufacturing, Inc.) equipped with round dies of 8 mm in diameter to obtain a swollen product. Soybean oil (5 parts by weight) and a fish extract (3 parts by weight) were sprayed onto the swollen product (92 parts by weight) to obtain dry cat food.

EXAMPLE 10

| Chicken meat | 74.9 parts by weight |
|---|---|
| Chicken viscera | 20 parts by weight |
| Vitamin/mineral mix | 5 parts by weight |
| AstaReal 50F | 0.1 part by weight |

The components listed above were blended by a mixer and cooked in a 2% saline solution at 100° C. for 10 minutes. The resultant cooked mixture was cooled and charged in cans to obtain canned dog food. The cans had a size of 75 mm of diameter and 110 mm of height. Each of the cans was charged with 300 g of meat together with 100 g of water. The cans were finally subjected to retort sterilization at a temperature 120° C. for 70 minutes.

EXAMPLE 11

| Cooked red meat | 93.9 parts by weight |
|---|---|
| Vitamin/mineral mix | 5 parts by weight |
| Calcium carbonate | 1 part by weight |
| AstaReal 50F | 0.1 part by weight |

The mixture of the aforementioned composition containing cooked red meat of skipjack and tuna as a main ingredient was prepared in flake form to obtain canned cat food. The cans had a size of 100 mm of diameter and 120 mm of height. Each of the cans was charged with 160 g of meat together with 100 g of water. The cans were finally subjected to retort sterilization at a temperature of 110° C. for 80 minutes.

When the pet food products prepared in Examples 6 to 11 were given to dogs or cats, they ate the food products without concern for smell and without hesitation. Furthermore, the same effect of deodorizing the excrement and effects of improving sleep, sensibility and visual sense as those in Example 5 were obtained.

The invention claimed is:

1. A method of deodorizing excrement in a pet, comprising administering to a pet in need of the deodorization of excrement at least one of astaxanthin and an ester thereof in an amount effective to deodorize excrement in the pet,
wherein the effective amount is 1 to 500 μg/kg body weight/day in terms of free astaxanthin.

2. The method according to claim 1, wherein the pet is at least one selected from the group consisting of a mouse, rat, guinea pig, rabbit, monkey, dog, cat, hamster, pig, cow, sheep, horse, crocodile, alligator, snake, lizard, and bird.

3. The method according to claim 1, wherein the pet is a dog or a cat.

4. The method according to claim 1, wherein the effective amount is 1.34 mg/day in terms of free astaxanthin.

* * * * *